US006000401A

United States Patent [19]

Herrick

[11] Patent Number: 6,000,401
[45] Date of Patent: Dec. 14, 1999

[54] ANATOMICAL APPARATUS FOR SUPPORTING A PERSON'S HEAD

[75] Inventor: Robert S. Herrick, Rialto, Calif.

[73] Assignee: Herrick Family Limited Partnership A California Limited Partnership, Rancho Cucamonga, Calif.

[21] Appl. No.: 08/951,694

[22] Filed: Oct. 16, 1997

[51] Int. Cl.$^6$ .......... A61B 19/00

[52] U.S. Cl. .......... 128/869; 5/637

[58] Field of Search .......... 128/845, 846, 128/869, 870; 602/17, 19; 5/630, 636, 637–645

[56] References Cited

U.S. PATENT DOCUMENTS

| | | | |
|---|---|---|---|
| 3,347,544 | 10/1967 | Uffenorde | 5/637 |
| 4,058,112 | 11/1977 | Johnson | 128/869 |
| 4,400,820 | 8/1983 | O'Dell | 128/869 |
| 4,612,678 | 9/1986 | Fitsch | 128/870 |
| 4,805,603 | 2/1989 | Cumberland | 5/644 |

*Primary Examiner*—Michael A. Brown
*Attorney, Agent, or Firm*—Daniel J. Meaney, Jr.

[57] ABSTRACT

An anatomical apparatus for supporting a head of a person by a person's mandible is shown. The anatomical apparatus includes a support defining a cavity having a lower tier of a selected width and an open upper wider tier communicating with the lower tier. A ledge or mandible engaging support surface is defined between the upper tier and lower tier and terminates in an exterior opening. The support is adapted to be positioned between a base of a head and shoulder of a person with the exterior opening positioned adjacent the shoulder when a person is in a supine position. The support urges the ledge or mandible engaging support surface into engagement with the mandible to support the head of person in a suspend position and to concurrently transport the mandible anterior of a person's body to maintain an open airway. A method for using the anatomical apparatus for suspending the head of a person is also shown.

21 Claims, 2 Drawing Sheets

ANATOMICAL APPARATUS FOR SUPPORTING A PERSON'S HEAD

BACKGROUND OF THE INVENTION

1. Field of the Invention

The invention relates generally to a device which positions and supports the head of a user for decreasing blockage of a person's air passageway or airway and more particularly relates an anatomical apparatus for suspending a body of a person by a person's mandible to transport the mandible anterior to a person's head to prevent blockage of a person's airway. The anatomical apparatus encourages maintenance of a person's airway and discourages or prevents partial or complete obstruction of the airway.

2. Description of the Prior Art

It is known in the art to utilize devices which attempt to prevent blockage of a person's airway. There are a number of applications for such devices including surgical applications, treatment of sleep apnea and snoring.

In surgical applications, an anesthesiologist is charged with the duties of administering drugs to alter the state of consciousness and of insuring that bodily functions are stabilized. During surgery, the anesthesiologist must assure that the patient spontaneously maintains vital functions, such as breathing, and if not then to intervene and control such vital functions. This may include intubation of the airway or air passageway (endotracheal intubation) or, in some instances, physically maintaining the patient in a position so that the patient can exchange air and breath via the actions of the functioning autonomic nervous system.

It is also known that the anesthesiologist can manually transport the mandible or jaw in a forward position which is the manual holding of the jaw must occur, accomplished by the anesthesiologist's using hands and fingers, sometimes for the duration of a surgical procedure.

Another known prior art problem which involves maintaining a person's airway is sleep apnea. Sleep apnea generally occurs when a person turns on the person's back while the person is asleep.

Typically, the force of gravity causes the jaw including the mandible to move posterially in relationship to the person's body. Posterior movement of the jaw compromises and partially or completely blocks the person's airway by mechanical obstruction. The person having a blocked airway does not breath until the carbon dioxide builds up to a point causing agitation. The person then responds to such agitation by making an exaggerated movement of the head, neck and possibly the shoulders to relieve the mechanical obstruction.

In addition to sleep apnea, snoring of a person involves some of the above described mechanisms. Further, during snoring, the uvula may add to the obstruction of the upper airway. Snoring may also be due to the presence of increased parasympathetic activity due to ocular surface disease from dry eye syndrome. It is known that increased parasympathetic activity causes congestion and constriction of a person's airway, principally the upper airway, as well as thickening of mucus secretions.

U.S. Pat. No. 5,123,132 discloses an anti-snoring pillow which reduces the snoring by the user when sleeping by positioning the head of the user at an angle reducing the degree of blockage. The user's pillow includes a base member which is preferably inclined and has a curved front edge which is lower in height than the rear edge. The upper surface of the base member is adjacent the front edge and has an elongated bolster secured thereto, which bolster is curved along its length to conform to the curved shape of the front edge of the base member. The bolster also includes a curved peripheral cross-sectional area for comfortable support of a user's neck. The bolster and the base member, and the choice of materials therefor act in conjunction to insure ensure comfort and also the positioning of a user's head so as to decrease the blockage of the user's breathing passageway when the user is in a back or in a side sleeping position.

The above described prior art devices and methods have certain deficiencies in successively eliminating blockage of a person's airway, sleep apnea and snoring.

During a surgical procedure, if an anesthesiologist utilizes the technique of physically or manually transporting the mandible anterior to a person's body in order to open an air passageway, the anesthesiologist's fingers and hand may become fatigued. If the surgical procedure is of a long duration, the anesthesiologist may be distracted from and(?) the anesthesiologist's other duties and obligations may be compromised due to the efforts required to maintain an open air passageway.

In the sleep apnea and snoring applications, a number of devices and procedures have been used to elevate a person's head or to otherwise maintain the head, neck, back, mouth and nose in predetermined positions to discourage blockage of a person's airway.

The anti-snoring device of U.S. Pat. No. 5,123,132, which is essentially in the form of a pillow attempts to maintain the elevation and/or position of the head at an angle to discourage blockage of a person's airway.

None of the known prior art devices disclose, suggest or teach the use of an anatomical apparatus having a mandible engaging support surface for using the weight of a person's head to develop a reactive force which transports the mandible anterior to the person's body to reduce or eliminate partial or complete blockage of a person's airway.

SUMMARY OF THE INVENTION

A novel, new and unique anatomical apparatus is disclosed and taught by the present invention which overcomes several problems associated with the prior art techniques and devices. In the preferred embodiment, the anatomical apparatus transports and supports a mandible of a person in a suspended position. The anatomical apparatus includes an integral support having a pair of spaced, opposed, generally vertically extending interior sidewalls having a selected length and defining a tiered, generally "U' shaped cavity extending over the selected length of the interior sidewalls. The generally "U" shaped cavity has a lower section of a selected width defining a bottom of the generally "U" shaped cavity and a wider upper section. A transitional mandible engaging support surface is formed in the vertically extending interior sidewalls and is located intermediate the lower section and the wider upper section. The mandible engaging support surface terminates in an exterior opening which communicates with the cavity. The integral support when positioned between a base of a head and shoulder of a person with the exterior opening positioned adjacent the shoulder when a person is in a supine position urges the mandible engaging support surface against the mandible to develop a reactive force in a direction which urges the mandible anterior in relation to the head while concurrently suspending the head to eliminate airway obstruction due to a posterior position of the mandible.

One advantage of the present invention is that the anatomical apparatus supports the head of a person in a suspended position while concurrently transporting the mandible anterior of a person's body to maintain an open airway.

Another advantage of the present invention is that the anatomical apparatus cavity can be generally "U" shaped cavity having a ledge which terminated in an exterior opening which enables the anatomical apparatus to be positioned under the head and neck with the exterior opening adjacent to the shoulders of a person.

Another advantage of the present invention is that the anatomical apparatus having a generally "U" shaped cavity is that the bottom of the cavity can be formed of a resilient member to cushion, position and stabilize the head of a person with the significant portion of head weight being supported by the mandible reacting with ledge or mandible engaging support.

Another advantage of the present invention is that the anatomical apparatus having a generally "U" shaped cavity can have the bottom of the cavity formed of a resilient member in the form of a inflatable member to cushion the head and neck of a person.

Another advantage of the present invention is that the anatomical apparatus can include a bottom of a "U" shaped cavity which terminates at a location beyond the person's neck and before a person's head and the bottom includes a shaped neck support to cushion, position and stabilize the neck of a person.

Another advantage of the present invention is that the ledge or mandible engaging support surface can be at a selected angle to position a person's head in a substantially horizontal position relative to the neck.

Another advantage of the present invention is that the ledge or mandible engaging support surface can be at a selected angle to position a person's head at a selected angle relative to the neck.

Another advantage of the present invention is that the anatomical apparatus may include a housing defining a cavity having at least one wall opening extending therethrough for receiving an insert having a cavity in the form of a generally "U" shaped hollowed-out area having a lower tier and an open upper wider tier communicating with the lower tier to define a ledge therebetween which functions as the mandible engaging support surface.

Another advantage of the present invention is that the anatomical apparatus can stabilize the head of a patient undergoing anesthesia.

Another advantage of the present invention is that the anatomical apparatus maintains a person's head at a substantially right angle to or normal to the rest of the person's body.

Another advantage of the present invention is that the anatomical apparatus tends to hyper-extend the head of a patient which encourages a patient's upper airway to remain open and unobstructed.

Another advantage of the present invention is that the anatomical apparatus can be utilized to hyper-extend the head of a patient to allow more readily accessible area of the face for performance of surgery such as, for example, eye surgery or facial surgery.

Another advantage of the present invention is that the anatomical apparatus is capable of selectively hyper-extending the head of a patient and the degree of hyper-extension and the angle thereof is determined by the structure of the anatomical apparatus.

Another advantage of the present invention is that the anatomical apparatus is capable of maintaining a person's airway in a selected position to prevent partial or complete obstruction of the person's airway. This has particular utility for aid persons who exhibit snoring problems, in the form of an anti-snoring device, or for reducing the adverse effects of persons who suffer from sleep apnea.

BRIEF DESCRIPTION OF THE DRAWINGS

These and other advantages of the invention will be readily apparent when considered in light of the detailed description hereinafter of the preferred embodiment and of the drawings which include the following figures.

DESCRIPTION OF THE PREFERRED EMBODIMENT

Figure 1:
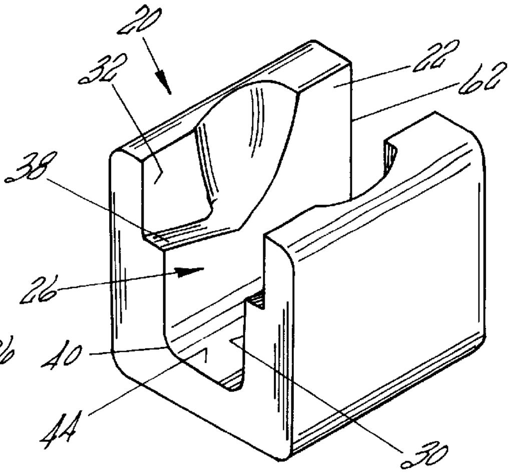
FIG. 1 is a top, front and right side perspective view of an anatomical apparatus for supporting the head of a person by a person's mandible.
Figure 2:
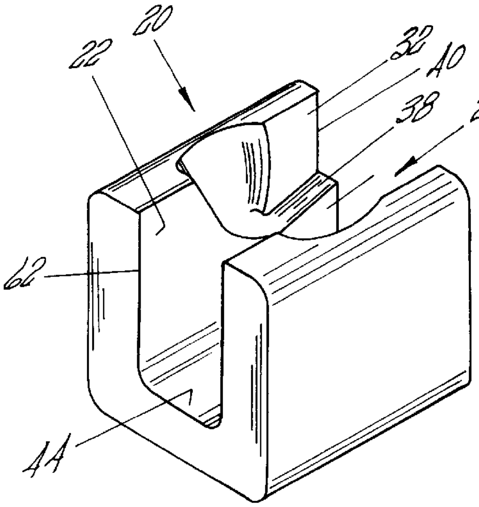
FIG. 2 is a top, rear and left side perspective view of an anatomical apparatus shown in FIG. 1.
Figure 15:
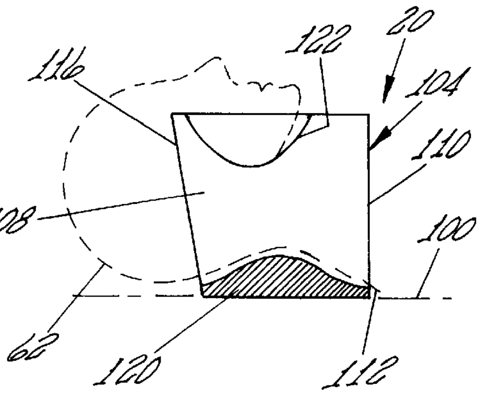
FIG. 15 is a pictorial representation partially in cross-section illustrating the structure of yet another anatomical apparatus wherein the length of the "U" shaped member terminates before the base of the head and after the neck and shoulders of a person in a supine position and wherein the bottom of the "U" shaped member includes a shaped neck support to cushion, position and stabilize the neck of a person.

FIGS. 1 and 2 disclose the preferred embodiment of an anatomical apparatus shown generally as 20 for supporting a head of a person by a person's mandible. FIGS. 3 through 7 disclose alternate embodiments of the anatomical apparatus shown generally as 20. FIGS. 8 through 14 show various species of an anatomical apparatus for cushioning the head of a person. FIG. 15 discloses yet another embodiment having a shaped neck support.

In FIGS. 1 through 7, the anatomical apparatus 20 includes a support 22 having a hollowed-out central area or cavity shown generally as 26 defined by substantially vertically extending sidewalls having a lower tier 30 of a selected width and an open upper wider tier 32 which communicates with the lower tier 30 to define a ledge on mandible engaging support surface 38 between the upper tier 32 and lower tier 30. The ledge or mandible engaging support surface 38 terminates in an exterior opening shown generally as 40. An opposed spaced second exterior opening shown generally as 62 is also formed which communicates with the substantially vertically extending sidewalls. The geometrical dimensions of the exterior openings are sized to accommodate a person's head.

The anatomical apparatus 20 is essentially an integral support 22 having a pair of spaced, opposed, generally substantially vertically extending interior sidewalls having a selected length and defining a tiered, generally "U' shaped cavity 26 extending over said selected length. The generally "U" shaped cavity 26 has a lower section 30 of a selected width defining the bottom 44 of the generally "U" shaped cavity 26 which communicates with the wider upper section 32.

The anatomical apparatus 20 illustrated in FIGS. 1 through 14 is adapted to be positioned under a person's neck and between a base of a head and shoulders of a person with the exterior opening 40 positioned adjacent the shoulder when a person is in a supine position. The weight of the person's head urges the ledge or mandible engaging support surface 38 into engagement with the mandible of a person to substantially support the head of a person in a suspended position while concurrently transporting the mandible anterior of a person's body to maintain an open airway.

In FIGS. 1 and 2, the ledge or mandible engaging support surface 38 is at a selected angle to support the mandible at a selected angle to position a person's head at a selected angle relative to a person's neck.

In FIGS. 3 through 7, the ledge or mandible engaging support surface 38 is at a selected angle to position a person's head at a substantially horizontal position relative to a person's neck. It is envisioned that the angle or length of the ledge or mandible engaging support surface 38 can be selected to be at any desired angle or length. For example, the angle could be in the range of about 0° to about 30°. A selected angle in the range of about 10° to about 20° is preferred.

Figure 13:
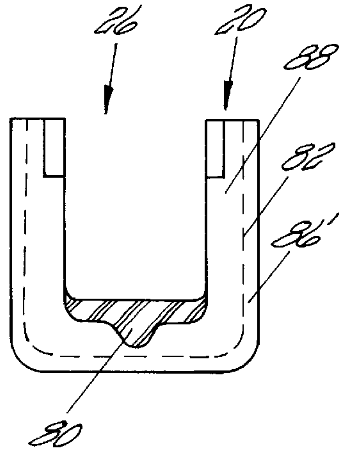
FIG. 13 is a front elevational view of yet another embodiment of an anatomical apparatus having a resilient material located at the bottom of the generally "U" shaped cavity to receive the head and neck of a person.
Figure 14:
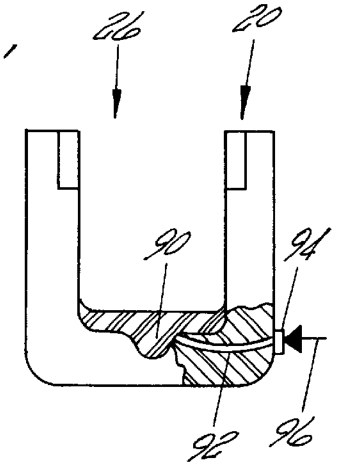
FIG. 14 is a front elevational view of still yet another embodiment of an anatomical apparatus having a resilient material in the form of an inflatable member located at the bottom of the generally "U" shaped cavity to receive the head and neck of a person.

As illustrated in FIG. 2, the cavity 26 is generally "U" shaped having a bottom 44 located at the lowermost portion of the generally "U" shaped cavity 26. In the embodiment illustrated in FIGS. 1 though 7, the bottom of the generally "U" shaped cavity 26 contacts and supports the head of a person. FIGS. 13 and 14 described herein below envisions and discloses that a resilient member can be located at the bottom 44 to receive, cushion and stabilize the head and neck of a person.

Figure 6:
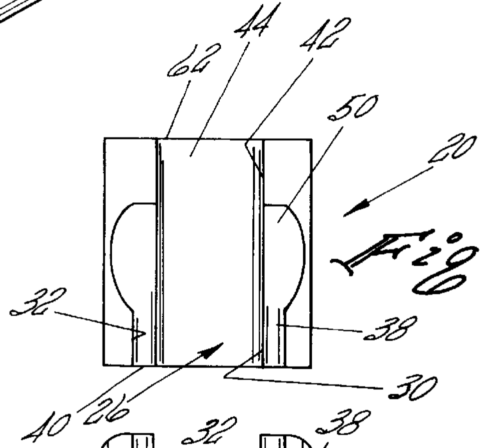
FIG. 6 is a top plan view of the anatomical apparatus illustrated in FIG. 3.
Figure 5:
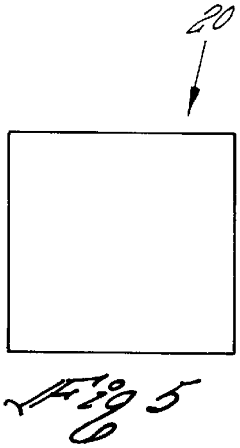
FIG. 5 is a left side plan view of the anatomical apparatus illustrated in FIG. 3.
Figure 3:
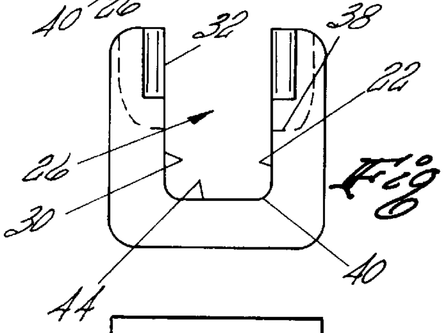
FIG. 3 is a front elevational view of the anatomical apparatus illustrated in FIG. 1 showing a ledge which functions as a mandible engaging surface and which positions a person's head at a substantially horizontal position relative to a person's neck.
Figure 4:
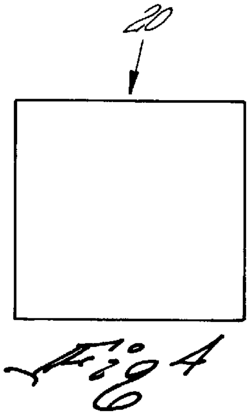
FIG. 4 is a right side plan view of the anatomical apparatus illustrated in FIG. 3.
Figure 7:
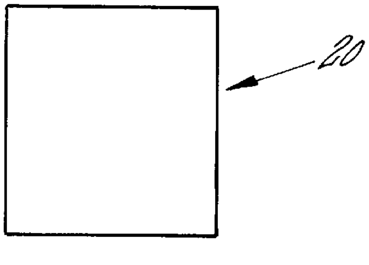
FIG. 7 is a bottom plan view of the anatomical apparatus illustrated in FIG. 3.

As discussed above, the embodiment of the anatomical apparatus illustrated in FIGS. 3 through 7 includes a mandible engaging support surface 38 which is formed to be substantially horizontal relative to a person's head. As illustrated in FIG. 6, the wider upper tier 32 has an enlarged area shown generally as 50 which is shaped or sized to receive and pass the ears of a person enabling the bottom of the head to slightly contact the bottom 44 of the generally "U" shaped cavity 26 with the ledge substantially supporting the person's head.

Figure 8:
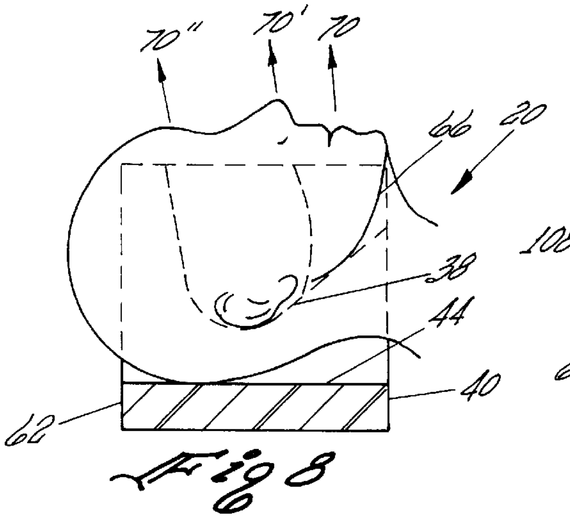
FIG. 8 is a pictorial representation partially in cross-section illustrating the position of the anatomical apparatus under a person's neck and between a base of a head and shoulders of a person in a supine position.

FIG. 8 illustrates pictorially the anatomical apparatus 20 being positioned under a person's neck and between the base of a head 60 of a person and the shoulders with two exterior openings 40 and 62 sized to receive the head 60. The mandible of a person, shown as 66, engages the ledge or mandible engaging support surface 38 suspending the head 60 thereagainst. The weight of the head 60 reacts with the ledge or mandible engaging support surface 38 to develop a reactive force in a direction which urges the mandible 66 anterior in relation to the head, the anterior direction being shown generally by arrow 70. The ledge or mandible engaging support surface 38 concurrently suspends the head 60 to eliminate airway obstruction which would otherwise occur if the mandible and root of a tongue is in a posterior position.

As illustrated in FIG. 8 the bottom 44 of the generally "U" shaped cavity 26 contacts and supports the head 60.

In FIG. 8, the selected angle of the ledge or mandible engaging support surface 38 is selected such that the head can be positioned either substantially perpendicular or normal to the person's body or neck or at a selected angle to the person's body or neck. By changing the angle of the ledge or mandible engaging support surface 38 to be at a larger selected angle, the mouth and head and root of a person's tongue can be rotated to the position shown as arrow 70". Conversely, by changing the angle of the ledge or mandible engaging support surface 38 to be at a smaller selected angle, the mouth and head can be rotated to the position shown as arrow 70'.

Figure 9:
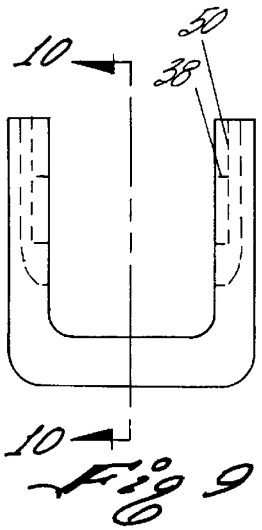
FIG. 9 is a front plan view of another embodiment of an anatomical apparatus having a ledge which functions as a mandible engaging surface and which is at a selected angle to position a person's head at a selected angle relative to a person's neck.
Figure 10:
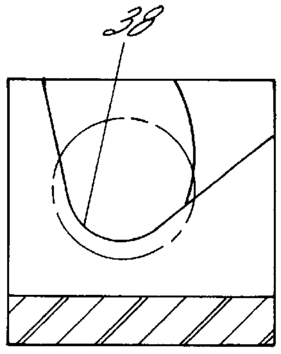
FIG. 10 is a sectional view taken along section lines 10—10 of FIG. 9.

FIGS. 9 and 10 illustrate pictorially that the ledge or mandible engaging support surface 38 can be contoured or shaped to accommodate a wide variety of mandibles and the size and dimensions of the enlarged area shown generally as 50 can selected to accommodate various size ears of a person.

Figure 11:
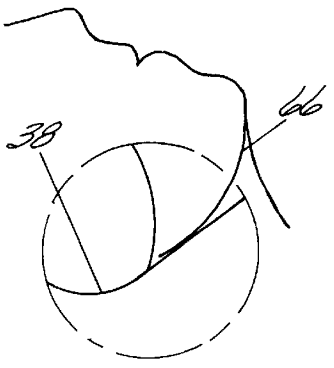
FIG. 11 is a pictorial representation illustrating the mandible engaging support surface being urged against the mandible to develop a reactive force in a direction which urges the mandible anterior in relation to a person's body in the supine position.

FIG. 11 illustrates a method for suspending the head of a person while concurrently transporting a person's mandible anterior to the person's body. FIG. 11 shows the step of positioning, under a person's neck and in a concave space located between a base of a head and shoulders of a person when a person is in a supine position, an anatomical apparatus 20 illustrated in FIG. 8 having a cavity having a lower tier of a selected width and an open upper wider tier communicating with the lower tier to define a ledge or mandible engaging support surface between the upper tier and wherein said ledge or mandible engaging support surface terminates in an exterior opening and lower tier and wherein said anatomical apparatus is adapted to be positioned under a person's neck and between a base of a head and shoulder of a person with the exterior opening positioned adjacent the shoulder when a person is in a supine position to urge the ledge or mandible engaging support surface into engagement with the mandible to support the head of person in a suspend position and to transport the mandible and root of a person's tongue anterior of a person's body to maintain an open airway; and suspending a person's head by reacting the ledge of the anatomical apparatus against the mandible to develop a reactive force at the ledge in response to a person's head weight, which reactive force is directed against and which transports the mandible and root of a person's tongue anterior to the person's body to prevent obstruction of a person's airway.

The method may further include the step of placing a person in a generally supine position. Also, the method may include in the step of positioning an anatomical apparatus having the ledge or mandible engaging support surface formed at a selected angle and further comprise the step of transporting the mandible at selected angle anterior to the person's body or neck.

In FIG. 11, ledge or mandible engaging support surface 38 is illustrated engaging with the mandible 66 to support the head 60 of person in a suspended position while concurrently transporting the mandible 66 and root of a person's tongue anterior of a person's body to maintain an open airway. The weight of the person's head reacts with the ledge or mandible engaging support surface 38 of the anatomical apparatus against the mandible to develop a reactive force at the ledge or mandible engaging support surface 38, which reactive force is directed against and which transports the mandible 66 and root of a person's tongue anterior to the person's body to prevent obstruction of a person's airway.

Figure 12:
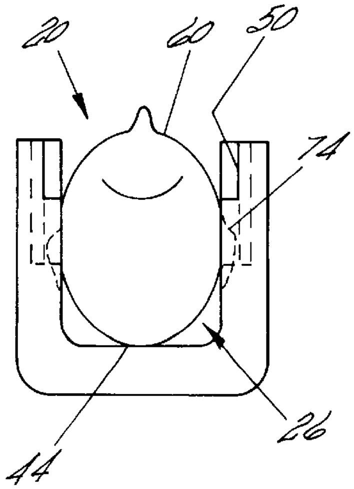
FIG. 12 is a pictorial representation from the front elevational view of the anatomical apparatus supporting a person's head to position the mandible against the mandible engaging support surface.

FIG. 12 pictorially illustrates how the head 60 of a person is located within the generally "U" shaped cavity 26 and with the ears 74 of a person 60 are located within the enlarged area shown generally as 50. In FIG. 12, the head 60 rests slightly against the bottom 44 since the mandible 66 substantially supports the weight of the head.

FIG. 13 illustrates an anatomical apparatus 20 wherein said bottom of the generally "U" shaped cavity 26 includes a resilient member 80 to receive and slightly support the head of a person. In the preferred embodiment, the resilient member is a resilient material.

In FIG. 13, dashed line 82 illustrates that the anatomical apparatus may comprise a housing shown by 86' having substantially vertically extending walls defining a cavity having a pair of said, opposed wall opening extending therethrough. An insert 88' is adapted to be positioned into the wall opening in the housing 86'. The insert 88' is fabricated to define a cavity having a lower tier of a selected width and an open upper wider tier communicating with said lower tier to define a ledge or mandible engaging support surface and wherein said ledge terminates in an exterior opening. The structure of the insert 88' may form in one of the structures associated with FIGS. 1 through 7 as described herein above.

FIG. 14 is yet another embodiment of an anatomical apparatus 20 having a generally "U" shaped cavity 26 wherein the resilient member is in the form of an inflatable member 90 which has a conduit 92 extending from an outlet 94 for inflating the inflatable member 90 with a fluid represented by arrow 96. The fluid may be air or water.

FIG. 15 diagrammatically illustrates an embodiment of an anatomical apparatus shown generally as 20, which has a structure to enable the base of the head 62 to rest on surface 100 located adjacent to the base of the head 62.

In FIG. 15, the anatomical apparatus 20 includes an integral support 104 having a pair of spaced, opposed, generally substantially vertically extending sidewalls 108. The sidewalls 108 have a first vertical edge 110, which is located near the shoulder 112 of a person, and a second, opposed slanted or sloped vertical edge 116, which is located near the base of the head 62. The generally substantially vertically extending sidewalls 108 have a selected length and define a tiered, generally a "U" shaped cavity which has a lower section defining a bottom 120, which is in the form of a shaped neck support having a surface which receives, cushions and supports the neck of a person.

In operation, the weight of person's head urges the ledge or mandible engaging support surface shown by dashed line 122 into engagement with the mandible of a person to substantially support the head of a person in a suspended position and provides support for the neck with the shaped bottom 120. The ledge or mandible engaging support surface 122 concurrently transports the mandible anterior of a person's body to maintain an open airway as discussed hereinbefore.

The ledge or a mandible engaging support surface 122 is formed at a selected angle, as described hereinbefore.

The materials which may be utilized for the construction or fabrication of the anatomical apparatus can be Styrofoam or other fairly soft semi-moldable plastic material. The anatomical apparatus would preferably be designed to be generally "U" shaped with two substantially vertically extending sidewalls connected by a substantially horizontal bottom portion which is substantially at right angles to or substantially perpendicular to the substantially vertically extending sidewalls. The angles of the sidewalls and bottom can be varied to accommodate injection moldings or thermoplastic molding techniques.

A one piece or integral structure is desired and can be fabricated for single use or multiple use application. Single use application may be preferable for surgical operations in that the anatomical apparatus can be disposed of upon completion of the surgical procedure to prevent possible contamination from body materials or fluids and to avoid the need for sterilization between procedures.

It is also envisioned, as described above in connection with FIG. 13, that the anatomical apparatus could be fabricated of two or more components one of which would be a housing and the other of which would be an insert to be positioned within the housing. Such a structure would have utility to provide for a multiple use housing member and use with for an insertable disposable, one time use insert permitting the insert to be disposed of after use which may have utility in a surgical applications.

The anatomical apparatus is adapted to be positioned posterior to the neck of the person in the concave space between the base of the skull and the shoulders. When the user is positioned on the user's back the anatomical apparatus is stabilized by the surface on which the patient is lying in a supine position. The angle of the jaw is engaged in the anatomical apparatus as described herein and the selected angle of the ledge or mandible engaging support surface automatically positions the jaw at a selected angle and concurrently moves the jaw forward.

In concept, the substantially vertically extending sidewalls are sized to fit or accommodate a person's head. The substantially vertically extending sidewalls are contoured in such a manner to define a "sling" to receive the mandible on each side thereof and, if desired to support the mandible at a selected angle. The area of contact is to be fabricated or formed so as to be smooth and to prevent any irritation to the skin in the area of contact. The area of contact may be fabricated to provide a sufficiently large area, on one hand, so as to provide a large surface-to-skin contact area to prevent any area of irritation to the regional skin, and, on the other hand, to have an appropriate width to receive and comfortably support the mandible.

The two substantially vertically extending sidewalls are interconnected to each other by a horizontal bridge of material, which essentially forms a bottom for the cavity.

The horizontal bridge of material is formed to be at substantially right angles to the substantially vertical extending sidewalls. This horizontal bridge of material passes under the neck of the person. The mandible reacts with the weight of the head which rests in the sling and which is in contact with and establishes the angle of the mandible. The resultant force developed between the mandible and sling urges the mandible into a more anterior position in relationship to the front surface area of the chest and relative to the head of the person. This results in the movement of the root of the tongue forward and thereby discourages or eliminates partial or total closure of the upper airway by the root of the tongue.

It is envisioned that the anatomical apparatus of the present invention can be used to maintain vital functions during sleep, surgery or sedation. In addition, the anatomical apparatus has utility as a device for treatment of sleep apnea. Also, the anatomical apparatus of the present invention can be considered as an anti-snoring apparatus. In application, the anatomical apparatus is essentially an anatomical mechanical support for the mandible to encourage maintenance of a patient airway and thereby discourage or prevent hypoxia. The anatomical apparatus of the present invention is capable of selectively moving the angle of the jaw of a person anterior to the person's body which in turn effects, moves, rotates and positions the root of the tongue in a manner to discourage or eliminate airway partial or complete obstruction.

The anatomical apparatus of the present invention has a wide variety of uses in the medical field, health care field, holistic health and for personal and home use to alleviate personal abnormalities such as sleep apnea and snoring.

The anatomical apparatus of the present invention has utility for secondary treatment of dry eye syndrome to help alleviate congestion and restriction of the upper airways due to increased parasympathetic hyperactivity. In certain applications the presence of increased parasympathetic activity due to ocular surface diseases may be aided by the anatomical apparatus as part of the overall treatment prognosis for dry eye syndrome.

It is also envisioned that variations in the structure of the anatomical apparatus are possible such as for example fabricating an anatomical apparatus specifically to fit a person's head in lieu of a structure that would be applicable for a variety of persons' head size. All such variations are anticipated to be within the scope of and teachings of the present invention.

What is claimed is:

1. An anatomical apparatus for supporting a head of a person to encourage maintenance of a person's airway comprising a support having a hollowed-out central area defined by substantially vertically extending interior side walls forming a lower section and a wider upper section and which includes a transitional mandible engaging support surface formed in the substantially vertically extending interior side walls and which is located intermediate said lower section and said wider upper section, said transitional mandible engaging support surface being adapted to be positioned in engagement with a mandible of a person to support the head of person in a suspend position and to concurrently transport the mandible anterior of a person's body to maintain an open airway.

2. The anatomical apparatus of claim 1 wherein said support is generally "U" shaped having a bottom and includes at the bottom thereof a resilient member to receive the head and neck of a person.

3. The anatomical apparatus of claim 2 wherein said resilient member is a resilient material.

4. The anatomical apparatus of claim 2 where said resilient member is an inflatable member.

5. The anatomical apparatus of claim 1 wherein said support is generally "U" shaped having a bottom and includes at the bottom thereof a shaped neck support to receive, support and cushion a person's neck.

6. The anatomical apparatus of claim 1 wherein said mandible engaging support surface is at a selected angle to position a person's head substantially horizontal relative to a person's neck.

7. The anatomical apparatus of claim 1 wherein said mandible engaging support surface is at a selected angle to position a person's head at a selected angle relative to a person's neck.

8. An anatomical apparatus for transporting and supporting a mandible and root of a tongue of a person in a suspended position, said apparatus comprising an integral support having a pair of spaced, opposed, generally vertically extending interior side walls having a selected length and defining a tiered, generally "U' shaped cavity extending over said selected length, said generally "U" shaped cavity having a lower section of a selected width defining a bottom of the generally "U" shaped cavity and a wider upper section; and a transitional mandible engaging support surface formed in the vertically extending interior side walls and located intermediate said lower section and said wider upper section, said support surface terminating in an exterior opening which communicates with said cavity;

said integral support when positioned between a base of a head and neck and shoulders of a person with the exterior opening positioned adjacent the shoulders when a person is in a supine position urges said mandible engaging support surface against the mandible to develop a reactive force in a direction which urges the mandible anterior in relation to the head while concurrently substantially suspending the head to eliminate airway obstruction which should otherwise occur if the mandible and root of the tongue is in a posterior position.

9. The anatomical apparatus of claim 8 wherein said bottom of the generally "U" shaped cavity includes a resilient member to receive the head and neck of a person.

10. The anatomical apparatus of claim 9 wherein said resilient member is a resilient material.

11. The anatomical apparatus of claim 9 wherein said resilient member is an inflatable member.

12. The anatomical apparatus of claim 8 wherein said bottom of the generally "U" shaped cavity includes a shaped neck support to receive, support and cushion a person's neck.

13. The anatomical apparatus of claim 8 wherein said mandible engaging support surface is at a selected angle to position a person's neck at a substantially horizontal position relative to a person's head.

14. The anatomical apparatus of claim 8 where said mandible engaging surface is at a selected angle to position a person's head at a selected angle relative to a person's head.

15. An anatomical apparatus comprising a housing having substantially vertically extending walls defining a cavity having spaced opposed wall opening extending therethrough;

an insert adapted to be positioned into said cavity and between said wall openings in said housing, said insert having a cavity having a lower tier of a selected width and an open upper wider tier communicating with said lower tier to define a ledge and wherein said ledge terminates in an exterior opening;

said support being adapted to be positioned posterior to a base of a person's head and between the neck and shoulders of a person with the exterior opening positioned adjacent the shoulders when a person is in a supine position to urge the ledge into engagement with the mandible to support the head of person in a suspended position and to concurrently transport the mandible and root of a tongue of a person anterior of a person's body to maintain an open airway.

16. The anatomical apparatus of claim 15 wherein said ledge defines a mandible engaging support surface which is formed to be substantially horizontal to horizontally transport the mandible.

17. The anatomical apparatus of claim 15 when said ledge defines a mandible engaging support surface which is formed at a selected angle to transport the mandible at a selected angle.

18. A method for suspending the head of a person while concurrently transporting a person's mandible anterior to the person's body comprising the steps of positioning under and between a base of a head and neck and shoulders of a person when a person is in a supine position an anatomical apparatus defining a cavity having a lower tier of a selected width and an open upper wider tier communicating with said lower tier to define a ledge between the upper tier and lower tier wherein said ledge terminates in an exterior opening and wherein said anatomical apparatus is adapted to be positioned between a base of a head and neck and shoulders of a person with the exterior opening positioned adjacent the shoulders when a person is in a supine position to urge the ledge into engagement with the mandible to support the head of person in a suspended position and to transport the mandible anterior of a person's body to maintain an open airway; and suspending a person's head by reacting the ledge of the anatomical apparatus against the mandible to develop a reactive force at the ledge in response to a person's head weight, which reactive force is directed against and which transports the mandible anterior to the person's body to discourage obstruction of a person's airway.

19. The method of claim 18 further comprising the step of placing a person in a generally supine position.

20. The method of claim 18 wherein the step of positioning has the ledge formed in the anatomical apparatus at a selected angle and further comprising the step of transporting the mandible at selected angle anterior to the person's body.

21. The method of claim 18 further comprising the step of positioning an anatomical apparatus having a shaped neck support located at the bottom of the "U" shaped cavity to receive, support and cushion the neck of a person.

* * * * *